United States Patent [19]
Alpern et al.

[11] Patent Number: 4,615,435
[45] Date of Patent: Oct. 7, 1986

[54] RETAINER FOR SURGICAL SUTURES

[75] Inventors: Marvin Alpern, Glen Ridge; Robert J. Cerwin, Pittstown; Constance E. Roshdy, No. Brunswick, all of N.J.

[73] Assignee: Ethicon, Inc., Somerville, N.J.

[21] Appl. No.: 810,959

[22] Filed: Dec. 19, 1985

[51] Int. Cl.⁴ .............................................. A61L 15/00
[52] U.S. Cl. .................................. 206/63.3; 206/476; 206/484; 206/628
[58] Field of Search .................... 206/63.3, 363, 227, 206/628, 476, 484; 128/335.5

[56] References Cited
U.S. PATENT DOCUMENTS

| 4,089,409 | 5/1978 | Cerwin | 206/63.3 |
| 4,120,395 | 10/1978 | Mandel et al. | 206/63.3 |
| 4,142,628 | 3/1979 | Marocco et al. | 206/63.3 |
| 4,182,448 | 1/1980 | Huck et al. | 206/63.3 |
| 4,254,862 | 3/1981 | Barratt | 206/63.3 |
| 4,496,045 | 1/1985 | Ferguson et al. | 206/63.3 |

Primary Examiner—Joseph Man-Fu Moy
Attorney, Agent, or Firm—Robert L. Minier

[57] ABSTRACT

An improved retainer for surgical sutures having a suture winding panel, suture holding panels, suture enclosing panel and retainer, interlocking panels. The panels of the retainer are folded to totally enclose the suture.

11 Claims, 6 Drawing Figures

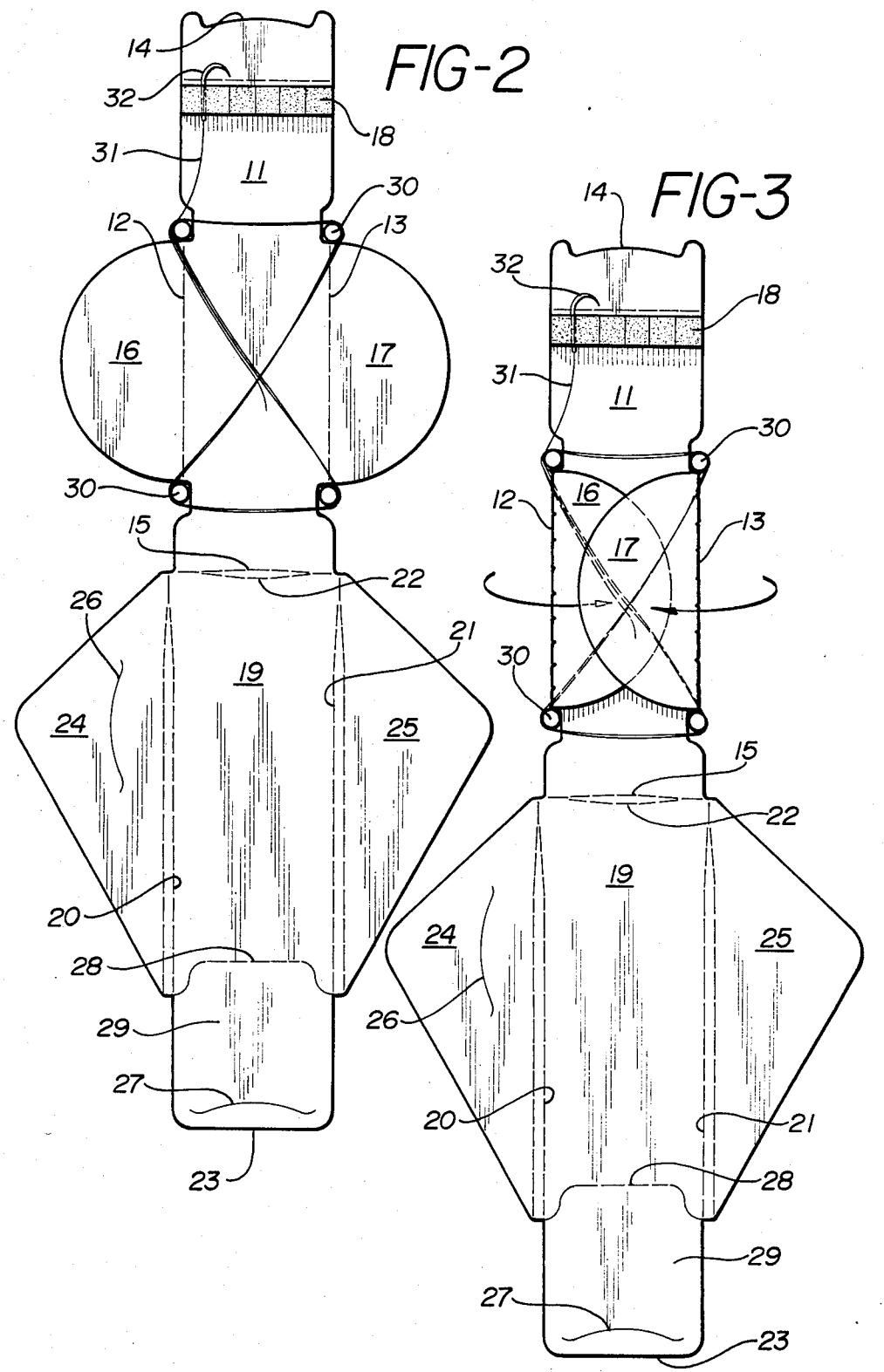

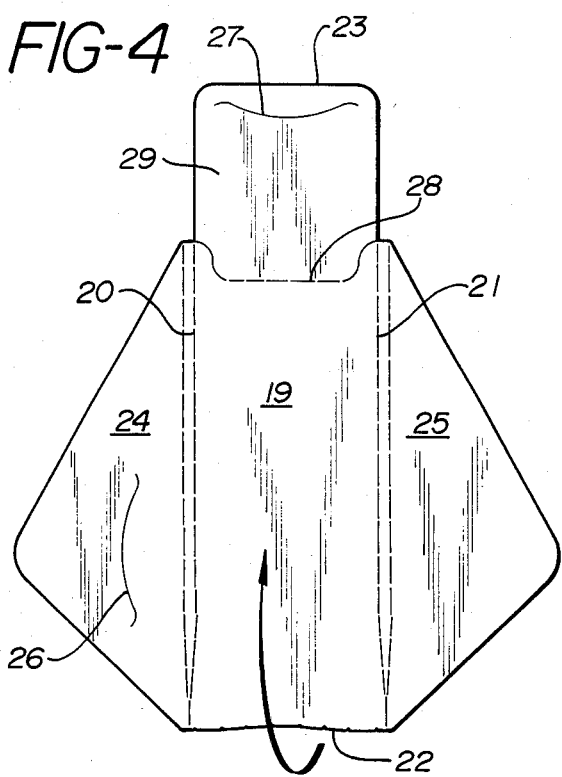
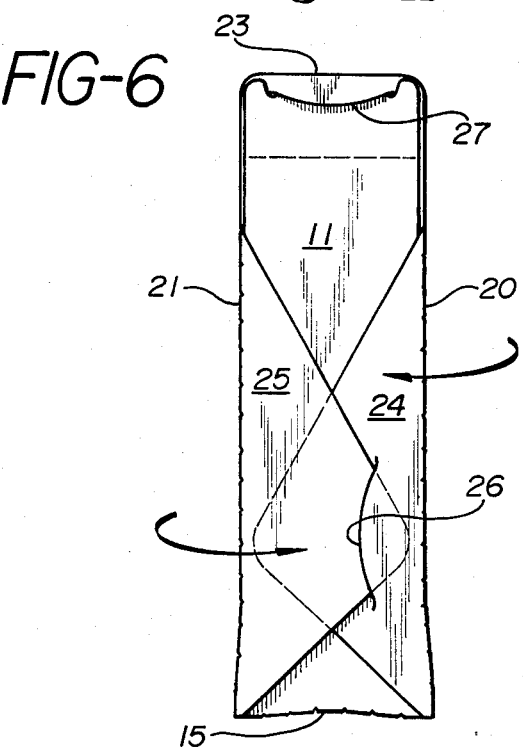
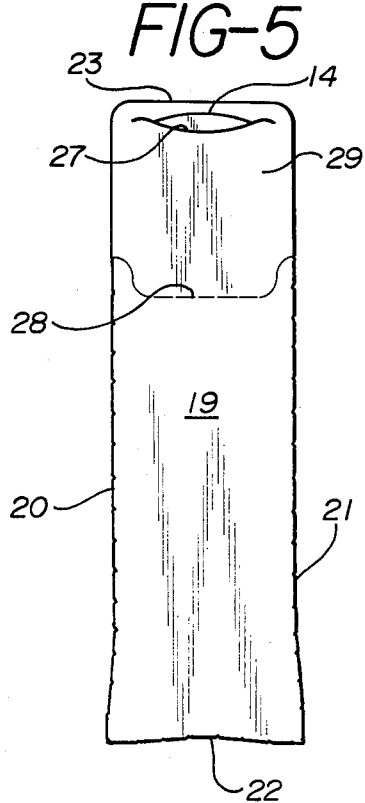

RETAINER FOR SURGICAL SUTURES

BACKGROUND OF THE INVENTION

The present invention relates to a retainer for surgical sutures and more particularly to a multiple panel retainer for securely holding surgical sutures.

Packages for surgical sutures are constructed according to the nature of the suture and its intended use. The packages are designed taking into consideration the economics of the package and the method of placing the sutures in the package. In general, the ideal package protects the suture during handling and storage yet allows the suture to be removed with the minimum of difficulty and the package itself should be economical to produce.

The more popular suture packages consist of a folded paper retainer with a suture therein and with the retainer contained in a sterile hermetically sealed envelope. In many instances, the sterility of the suture in the envelope is maintained by a second sealed outer wrap. When the suture is to be used, the outer wrap is opened in the operating room and the sealed envelope deposited in the sterile area. Sterile personnel thereupon tear open the sterile envelope to gain access to the suture.

Many packages have been developed to provide: easy access to the sutures, simplified winding of the suture, dispensing of a single suture from a package containing multiple sutures, and the like. Representative packages are more fully described in U.S. Pat. Nos. 3,936,696, 3,280,971, 3,490,192, 4,089,409, 4,126,221, 4,253,563, 4,249,656, 4,491,218, 4,483,437, 4,413,727, 4,412,614, 3,985,227, and 4,120,395.

As mentioned above, packages for surgical sutures are often constructed according to the nature of the suture being packaged. For example, if the suture is made from material that is heat sensitive it is important the package totally enclose the suture to protect it from heat during the sterilization or storage of the suture. If the suture is made from a monofilament material; i.e., a material which tends to take a set in a configuration which is held for any period of time, the package should be designed to take that property into consideration. Also, suture packages should be designed for efficiency in use; i.e., when the nurse is opening a suture package in the surgical environment, the nurse should have control of the opening of the package and the package should not open prematurely of unwarrantedly. It is desirable that the package be easily opened and in many instances opened using one hand, i.e. the package held in the hand and readily opened by a finger because the other hand of the person who desires to open the package may be occupied.

The present invention presents a very simple suture package. The package is inexpensive to produce and the method for placing sutures in the package and folding the package are simple and economical. The package totally encloses the suture and may be used with heat sensitive suture materials. It is an object of the present invention to produce a package that can hold monofilament sutures in as gentle curves as possible to avoid undue set of the suture. A further object of the present invention is to provide a suture package that is securely locked and will not open inadvertently. It is yet a further object of the present invention to provide a suture package which the user may readily open utilizing only one hand. These and other objects of the present invention will be apparent from the ensuing description and claims.

SUMMARY OF THE INVENTION

The present invention provides an improved retainer for surgical sutures. The retainer has a suture winding panel with the panel having a pair of longitudinal edges and a pair of transverse ends. The retainer includes a pair of suture holding panels foldably connected to longitudinal edges of the suture winding panel with one of the holding panels connected to one longitudinal edge of the winding panel and the other holding panel connected to the opposite longitudinal edge of the suture winding panel. The holding panels extend only along a portion of the suture winding panel so that a suture which is wound on the winding panel will extend beyond the ends of the holding panels. The retainer includes a suture enclosing panel which has a pair of longitudinal edges and a pair of transverse edges. One of the suture enclosing panel's transverse edges is foldably connected to a transverse edge of the suture winding panel. The retainer also includes a pair of retainer interlocking panels foldably connected to the longitudinal edges of the suture enclosing panel with one of the retainer interlocking panels foldably connected to one longitudinal edge of the enclosing panel and the other retainer interlocking panel connected to the other longitudinal edge of the enclosing panel. The retainer is used by winding a suture on the suture winding panel. The pair of suture holding panels are folded on top of the wound suture to hold the suture in place. The suture enclosing panel is folded on top of the suture holding panels and the retainer interlocking panels folded behind the suture winding panel and interlocked together to hold the folded panels in their folded configuration. In certain embodiments of the present invention there is a needle holding means, such as a piece of foam, placed at the free end of the suture winding panel on the same side of the suture panel on which the suture is to be wound. The needle(s) of either a single or a double armed suture may be inserted in this holding means so that the needle is held in place. In other embodiments of the present invention the free end of the suture enclosing panel is deflectable so that it may be readily displaced away from the suture enclosing panel to expose a portion of the suture and in many instances the needle attached to the suture. In other embodiments of the present invention, the fold lines include gussets to reduce pressure being placed on the suture in handling the folded retainer. In still other embodiments of the present invention, there is a slot placed at the free end of the suture winding panel and a complimentary tab placed at the free end of the suture enclosing panel so the free ends of the winding panel and the enclosing panel may be interlocked to even further lock the folded retainer in place. The invention will be more fully described in conjunction with the accompanying drawings.

DESCRIPTION OF THE DRAWINGS

FIG. 2 is a plan view of the improved retainer of FIG. 1 showing a needle and suture disposed on the suture winding panel;

FIG. 3 is the retainer of FIG. 2 showing the suture holding panels folded on top of the suture;

FIG. 4 is a plan view of the retainer of FIG. 3 showing the suture enclosing panel folded on top of the suture holding panels;

FIG. 5 is a plan view of the retainer of FIG. 4 in its fully folded condition; and FIG. 6 is a plan view showing the opposite surface of the retainer of FIG. 5 with the interlocking retainer panels folded and locked in position;

DETAILED DESCRIPTION OF THE DRAWINGS

Figure 1:
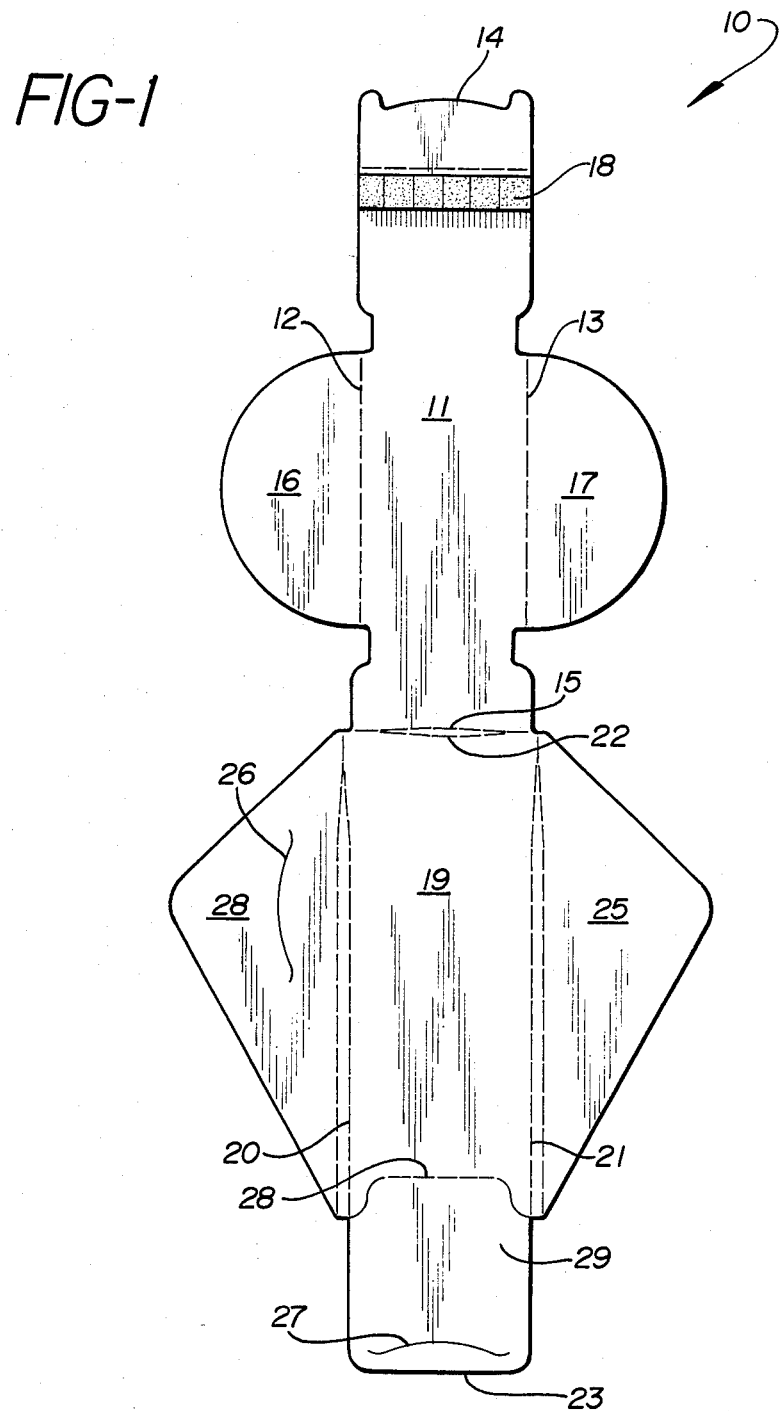
FIG. 1 is a plan view of the improved retainer of the present invention.

FIGS. 1-6 illustrate the various stages in preparing and folding the retainer of the present invention. Similar features of the retainer are designated by the same number throughout the drawings. The term "suture" when used in this application relates to both a needle or unneedled strand of suture material.

In FIG. 1 there is depicted an unfolded suture retainer 10 of the present invention. The retainer comprises a suture winding panel 11 which is generally rectangular in shape and has a pair of longitudinal side edges 12 and 13 and a pair transverse ends 14 and 15. Foldably connected to each side edge is a semicircular shaped suture holding panel 16 and 17. The straight side of the semicircular suture holding panel is foldably connected to the longitudinal edge of the suture winding panel. Adjacent to the free transverse end of the suture winding panel is a foam member 18. This member holds needles attached to the suture. The free transverse end of the suture winding panel is slightly arched i.e. it is slightly concave for improved interlocking of the folded retainer as will be hereinafter described. Foldably connected to the opposite transverse end of the suture winding panel is the suture enclosing panel 19. This panel is rectangular in shape and is substantially coextensive with the suture winding panel when folded. This suture enclosing panel has a pair of longitudinal sides edges 20 and 21 and a pair of transverse ends 22 and 23. Foldably connected to each longitudinal side edge is a retainer interlocking panel 24 and 25. The retainer interlocking panels are triangular in shape with the long side of the triangles foldably connected to the longitudinal edge of the suture enclosing panel. One of the retainer interlocking panels has a slit 26 which is used to interlock with the free end of the opposite interlocking retainer panel as will be hereinafter described. Disposed adjacent the free transverse end of the suture enclosing panel is a complimentary slit 27 which engages with the free end of the suture winding panel when the retainer is folded as hereinafter described.

In a preferred embodiment the fold lines between the suture winding panel and the suture enclosing panel and the fold lines between the suture enclosing panel and the interlocking retainer panels are dual fold lines to provide gussets between the enclosing panel and the suture winding panel. These gussets prevent undue pressure from being placed on the suture in the retainer and allow the suture to be readily removed from the retainer and not held therein by excess friction.

The suture enclosing panel also includes a scored line 28 to provide a deflectable end portion 29 of the suture enclosing panel. Referring to FIG. 2 there is shown the retainer of FIG. 1 which has been placed on four pins 30. The pins are adjacent the longitudinal side edges of the suture winding panel and just outside the semicircular holding panels. Positioning the pins in this manner elminates opening or holes in the retainer and, hence, the panel may totally contact the suture and protect the suture during sterilization, storage, transportation and the like. As shown in FIG. 2, the suture 31 with the needle 32 attached is wound about the pins in a figure 8 configuration. The suture may be wound about the pins in other desired configurations. In winding the suture, the needle is first placed in the needle holding member and the suture wound about the pins with the free end of the suture disposed in the center of the suture winding panel.

Once the suture has been wound, the two suture holding panels are folded on top of the wound suture as shown in FIG. 3. Once the suture holding panels are folded over the suture to hold the suture in place the retainer may be removed from the pins. It should be noted that by placing the pins outside the suture winding panel very gentle curves may be obtained in winding the suture and the propensity for placing an undesirable set in monofilament sutures is reduced.

As is shown in FIGS. 4 and 5, the suture enclosing panel is then folded on top of the suture holding panels. The pair of interlocking retainer panels are folded behind the suture winding panel and interlocked by placing the free end of one of the interlocking retainer panel in the slit of the other interlocking retainer panels as shown in FIG. 6. To fully lock the retainer in place, the slightly arched transverse free end of the suture winding panel is interlocked with the slit at the transverse free end of the suture enclosing panel as shown in FIG. 5.

Referring to FIGS. 1 and 2, adjacent the ends of the interlocking retainer panels closest to the free end of the suture enclosing panel there is a scored area 28 extending transversely of the suture enclosing panel. The purpose of this scored portion will be hereinafter described. The folded retainer shown in FIGS. 5 and 6 with the suture therein may then be wrapped in a suitable foil-film overwrap as is well known in the art and sterilized by any of the techniques well known in the art depending on the type of suture material used. As can be appreciated, this is a simple and economical package to produce. The package totally encloses and protects the suture and the needle, yet it is a simple matter to hold the package in one hand, unlock the interlocking tab at the transverse ends of the suture winding panel and the suture enclosing panel and fold back the scored portion of the suture enclosing panel with the same fingers of the hand holding the retainer. This allows ready and simple one handed access to the suture in the package.

The package does not contain holes and, hence, is inexpensive to produce, produces no debris and makes the entire operation very economical.

The interlocking retainer panels and the locking at the transverse ends of the suture winding panel and the suture holding panel make a very secure folder as compared to most folded retainers which have side locks in the foldable portion of the suture retainer. By placing the locking means in the positions as shown in FIGS. 5 and 6, this folder will not open when the nurse or surgeon goes to use the folder.

With the two suture holding panels positioned inside the pins, once the suture is wound and held in place by folding these panels on top of the suture, the suture is under control and when the retainer is removed from the pins the suture remains under control and will not be damaged by having an end of the suture hung up on a panel or a pin and the like. Furthermore, by eliminating the side locks, the possibility of a portion of the suture getting caught in one of these locks and being damaged is also eliminated.

The arched portion of the suture winding panel allows for a space between the panels of the needle holder and eliminates undue stress on the needle holder while still retaining a very secure lock. As previously mentioned, the fully folded suture retainer may be subsequently sealed and sterilized within a sterile outer envelope. Generally, these envelopes are formed by heat sealing two coextensive panels; for example, one of a non-woven fabric and the other of a thermoplastic film coated on their interior surface with a heat sealable polymeric composition, together about their periphery. The laminate is bonded together about the periphery with the retainer within this periphery. Other means for sealing an envelope may be used at the discretion of the practioner. If desired, an indentation or gore may be placed in the outer envelope to aid in tearing open that envelope to expose the folded retainer. The sutures so packaged are sterile and hermetically sealed and may be stored for extended periods of time.

The suture retainers of the present invention are preferably constructed of a heavy-weight relatively stiff sulfate paper board. This paper board is relatively foldable and yet sufficiently strong and stiff to support the suture and provide a rigid package. Other materials including plastics, foils, and laminates combined with each other or with paper may also be used.

The preceeding description has been primarily to a preferred embodiment of the present invention and many variations which nevertheless employ the features thereof will be apparent to those skilled in the art. Such variations are included within the scope of the present invention.

What is claimed is:

1. An inproved retainer for surgical sutures comprising:
   a. A suture winding panel having a pair of longitudinal edges and a pair of transverse edges,
   b. a pair of suture holding panels, an edge of one of said suture holding panels being foldably connected to a longitudinal edge of said suture winding panel and an edge of the other of said suture holding panels being foldable connected to the opposite longitudinal edge of said suture winding panel, said foldably connected edges of said suture holding panels extending along only a portion of the longitudinal edges of said suture winding panels whereby portions of a suture wound on said suture winding panel extend beyond the foldably connected edges of said suture holding panels,
   c. a suture enclosing panel having a pair of longitudinal edges and a pair of transverse edges, a transverse edge of said suture enclosing panel being foldably connected to a transverse edge of said suture winding panel,
   d. a pair of retainer interlocking panels, an edge of one of said retainer interlocking panels being foldably conntected to a longitudinal edge of said suture enclosing panel and an edge of the other said retainer interlocking panel being foldably connected to the opposite longitudinal edge of said suture enclosing panel, whereby a suture may be wound on said suture winding panel, held in place by folding said suture holding panels on top of said wound suture, enclosed by folding said suture enclosing panel on top of said suture holding panels and the folded panels locked in their folded condition by folding said retainer interlocking panels behind said suture winding panel and interlocking said retainer interlocking panels.

2. An improved retainer for surgical sutures according to claim 1 wherein needle holding means is disposed adjacent the transverse edge of the suture winding panel opposite the transverse edge foldably connected to the suture enclosing panel.

3. An improved retainer for surgical sutures according to claim 1 wherein the free end of said suture enclosing panel has a hinged portion which may be deflected away from the remainder of said suture enclosing panel to expose a suture wound on the suture winding panel.

4. An improved retainer for surgical sutures according to claim 1 wherein the fold lines connecting the suture winding panel to the suture enclosing panel and the fold lines connecting the interlocking retainer panels to the suture enclosing panels are dual fold lines to form gussets between said fold lines.

5. An improved retainer for surgical sutures according to claim 1 wherein the suture winding panel is continuous.

6. An improved retainer for surgical sutures according to claim 1 wherein the suture winding panels are semicircular in shape.

7. An improved retainer for surgical sutures according to claim 1 wherein the retainer interlocking panels are triangular in shape.

8. An improved retainer for surgical sutures according to claim 1 wherein one of the retainer interlocking panels has a slit disposed in said panel for engaging the free end of the other retainer interlocking panel to interlock the folded retainer.

9. An improved retainer for surgical sutures according to claim 1 wherein the free end of the suture enclosing panel has a transverse slit thereto for engaging with the free end of the suture winding panel to lock the folded retainer in place.

10. An improved retainer for surgical sutures according to claim 9 wherein the free end of the suture winding panel is concave.

11. An improved retainer for surgical sutures according to claim 1 wherein there is a needle holding means disposed adjacent the free transverse end of the suture winding panel, the free end of the suture enclosing panel not foldably connected to said suture winding panel is deflectable to expose a portion of a suture wound on the suture winding panel when the retainer is folded, the fold lines are dual fold lines forming gussets, the suture holding panels are semicircular in shape, the retainer interlocking panels are triangular in shape and one of said retainer interlocking panels contains a slit which when the retainer is folded accepts the free end of the other retainer interlocking panel to lock the folded retainer.

* * * * *